United States Patent [19]

Speier

[11] 4,082,790

[45] Apr. 4, 1978

[54] METHOD OF PREPARING MERCAPTANS

[75] Inventor: John L. Speier, Midland, Mich.

[73] Assignee: Dow Corning Corporation, Midland, Mich.

[21] Appl. No.: 557,214

[22] Filed: Mar. 10, 1975

Related U.S. Application Data

[63] Continuation-in-part of Ser. No. 531,831, Dec. 11, 1974, abandoned.

[51] Int. Cl.$^2$ ............................ C07F 7/08; C07F 7/18
[52] U.S. Cl. ................................. 260/448.8 R; 560/9; 560/147; 260/448.2 E; 260/448.2 N; 260/514 R; 260/515 M; 260/593 R; 260/590 B; 260/611 A; 260/614 R; 260/618 R; 260/632 R; 260/609 R
[58] Field of Search ................ 260/448.2 E, 448.8 R, 260/514 R, 515 M, 470, 481 R, 590, 593 R, 611 A, 614 R, 618 R, 632 R, 609 R

[56] References Cited

U.S. PATENT DOCUMENTS

| 3,590,065 | 6/1971 | Rakus et al. | 260/448.8 R |
| 3,856,842 | 12/1974 | Nagai et al. | 260/448.2 E |

OTHER PUBLICATIONS

Simpson, "Canadian Journal of Research", Section B, vol. 25, pp. 20–27 (1947).

Primary Examiner—Paul F. Shaver
Attorney, Agent, or Firm—Robert F. Fleming, Jr.

[57] ABSTRACT

Mercaptans are prepared by reacting an organic chloride or bromide with a mixture of $H_2S$ and ammonia or an amine at a temperature of 0° to 175° C. under autogenous pressure. The reaction can be carried out in the presence of a polar solvent. For example, 3-chloropropyltrimethoxysilane is mixed with $H_2S$ and ammonia in methanol and heated in a closed container at 100° C. for 18 hours.

10 Claims, No Drawings

METHOD OF PREPARING MERCAPTANS

This application is a continuation-in-part of my application Ser. No. 531,831, filed Dec. 11, 1974, now abandoned.

One of the problems encountered during the preparation of mercaptans by most of the common commercial methods is the formation of by-produced sulfides. This occurs both when $H_2S$ is added to unsaturated compounds and when the heretofore employed alkali metal hydrosulfides are reacted with chlorides or bromides. The reason for the formation of sulfides in the first process is because the mercaptan adds to a double bond more rapidly than the $H_2S$. With respect to the hydrosulfide reaction, all alkali metal hydrosulfides contain alkali metal sulfides. These give rise to the organic sulfide by-product. Another method which has been employed for the production of mercaptans is shown in U.S. Pat. No. 3,590,065. This involves the the reaction of an organic halide with thiourea in the presence of ammonia. The products are the mercaptan and guanidine hydrochloride which is voluminous in character and imposes a serious disposal problem.

It is known from U.S. Pat. No. 3,849,471 that mercaptoalkyl silicon compounds can be prepared by reacting chloroalkylsubstituted silicon compounds with $H_2S$ in the presence of ethylene diamine. This patent shows column 9, Example 13, runs 22 to 25 that amines such as tributyl amine, pyridine and diethylene triamine do not cause the reaction to go to any significant extent. It is, therefore, most unexpected that ammonia and the amines of this invention cause the reaction to proceed in excellent yields.

It is an object of this invention to provide a novel method for preparing mercaptans which, under the right conditions, avoids the formation of any significant amount of sulfide and which at the same time uses cheap reagents. Thus, this invention represents an advance in the art of preparing mercaptans which gives economic advantages over prior processes.

This invention relates to a method of producing mercaptans which comprises reacting (A) a halide of the formula $RX_a$ with a mixture of (B) ammonia or a hydrocarbyl amine containing one N atom, no more than 6 carbon atoms and being free of aliphatic unsaturation and having a $K_a$ of less than $1 \times 10^{-9}$ in aqueous solution, and $H_2S$, in the mole ratio of at least one mole of $H_2S$ and one mole of (B) per mole of halogen in (A) at a temperature of from 0° to 175° C. under autogenous pressure whereby a compound of the formula $R(SH)_a$ is formed, in which process R is selected from the group consisting of aliphatic, cycloaliphatic or aralkyl hydrocarbon radicals free of aliphatic unsaturation, such hydrocarbon radicals substituted with alkoxy, keto, carboxyl, hydroxyl, —$COOR^3$ or —$OOCR^3$ in which $R^3$ is a monovalent hydrocarbon radical free of aliphatic unsaturation, and silylated hydrocarbon radicals of the formula $(R''O)_yR'''_{3-y}SiR^4$— or $(O_{3-d/2})R'''_dSiR^4$— in which R'' is an alkyl or an alkoxyalkyl radical of 1 to 6 carbon atoms, R''' is a monovalent hydrocarbon radical free of aliphatic unsaturation, a haloaryl radical or $R_fCH_2CH_2$— in which $R_f$ is a perfluoroalkyl radical, $R^4$ is a divalent or trivalent aliphatic, cycloaliphatic or aralkyl radical free of aliphatic unsaturation, y is 1 to 3, and d is 0 to 2, X is bromine or chlorine, and a is 1 to 3.

It can be seen that the halide reactant (A) can contain 1, 2 or 3 halogen atoms and that these can be chlorine or bromine or a combination thereof. The halogen atom is attached to an aliphatic or cycloaliphatic carbon atom and R is free of aliphatic unsaturation. R then, can be any alkyl radical such as methyl, ethyl, propyl, isopropyl, hexyl or octadecyl, or any cycloaliphatic hydrocarbon radical such as cyclopentyl, cyclobutyl, cyclohexyl or methylcyclohexyl, or any aralkyl hydrocarbon radical such as benzyl, beta-phenylethyl, 2-phenylpropyl, beta-xenylethyl, gamma-naphthylpropyl and the like. Typical halides, then, are ethylchloride, 1,3-propylenedibromide, 1,2,3-trichloropropane and 1-chloro-3-bromocyclohexane.

In addition, the reactant (A) can be substituted with one or more of the defined substituents so that (A) can be a haloether such as chloromethylmethyl ether, chloroethylethyl ether, bis-chloromethyl ether, chlorobutylmethyl ether, chloromethylphenyl ether or chloromethylbenzyl ether; or halogenated ketones such as bromomethylmethyl ketone, chloromethylethyl ketone, chloromethylphenyl ketone, chloroethylbenzyl ketone or bis-chloroethyl ketone; halogenated carboxylic acids such as chloro acetic acid, alpha-chloropropionic acid, beta-bromopropionic acid, gamma-chlorobutyric acid, or chlorocyclohexyl carboxylic acid. It should be understood, of course, that the products formed by the reaction of a halogenated acid produces the corresponding ammonium or amine salt. The free acid can be obtained by reacting this salt with a strong acid such as hydrochloric, etc. In addition, (A) can be a halo alcohol such as beta-chloroethanol, beta-chloropropanol, or bromohexanol. (A) can be an ester of a halogenated carboxylic acid which ester contains the group —$COOR^3$ in which $R^3$ is a monovalent hydrocarbon radical such as methyl, ethyl, isopropyl, butyl, phenyl, cyclohexyl or benzyl or (A) can be a carboxylic acid ester of a halo alcohol which ester contains the group —$OOCR^3$ in which $R^3$ is as above described.

In addition, (A) can be a silane of the formula $(R''O)_yR'''_{3-y}SiR^4$— or a siloxane of the formula $(O_{3-d/2})R'''_dSiR^4$— in which silanes and siloxanes R'' is any alkyl radical such as methyl, ethyl, isopropyl, butyl or hexyl or any alkoxyalkyl radicals such as —$OCH_2CH_2OCH_3$ or $O(CH_2CH_2O)_2C_2H_5$ and R''' is any monovalent hydrocarbon radical free of aliphatic unsaturation such as methyl, ethyl, isopropyl, butyl, phenyl, xenyl, naphthyl, benzyl, beta-phenylethyl, 2-phenylpropyl, or cyclohexyl; any haloaryl radical such as chlorophenyl, dichlorophenyl, chloroxenyl, or chloroanthracyl, or fluorinated hydrocarbon radicals of the formula $R_fCH_2CH_2$— in which $R_f$ is any perfluoroalkyl radical such as perfluoromethyl, perfluoroethyl, perfluorobutyl, perfluoroisobutyl or perfluorooctyl. The divalent radical $R^4$ between the halogen and the silicon can be any divalent aliphatic hydrocarbon radical such as methylene, dimethylene, trimethylene, isobutylene or octadecamethylene or any cycloalkylene radical such as cyclohexylene, methylcyclohexylene, cyclopentylene or cyclobutylene or any aralkylene radical in which the silicon is attached to the aromatic ring, such as benzylene, —$C_6H_4CH_2CH_2$—,

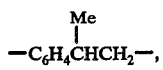

or —CH$_2$CH$_2$C$_6$H$_4$CH$_2$—. R$^4$ can also be trivalent or tetravalent radicals of the above type in which case $a$ has a value of 2 or 3 respectively.

The siloxanes employed as reactants can be homopolymers or copolymers and they can have either 1, 2 or 3 organic radicals substituted on the silicon atom. Also these siloxanes can contain some silicon-bonded hydroxyl groups and some copolymerized organosiloxane units, which are free of reactive halogenated units, of the formula R'''$_z$SiO$_{(4-z/2)}$ in which R''' is as above defined and $z$ is 0 to 3, such as, for example, dimethylsiloxane units, phenylmethylsiloxane units, trimethylsiloxane units, trifluoropropylmethylsiloxane units, diphenylsiloxane units, monophenylsiloxane units, monomethylsiloxane units, or SiO$_2$ units. Of course, in these copolymers there should be at least one siloxane unit having the defined —R''X$_a$ substituents. Such copolymers are considered within the process of this invention.

Reactant (B) employed in this invention can be ammonia or any hydrocarbon amine containing one N atom and no more than 6 carbon atoms which is free of aliphatic unsaturation and has a K$_a$ of less than 1 × 10$^{-9}$. This means that the amines are those in which the nitrogen is attached to aliphatic or cycloaliphatic carbon atoms. Specific examples of such amines are primary amines such as methyl amine, butyl amine, isopropyl amine, cyclohexyl amine and cyclopentyl amine; secondary amines such as dimethyl amine, dipropyl amine and methylbutyl amine and tertiary amines such as trimethyl amine, triethyl amine or ethyldimethyl amine. The total number of carbon atoms in the amine should be no more than 6.

The mole ratio of (B) to H$_2$S is not critical since either can be in large excess over the other. However, for best results there should be at least one mole of H$_2$S and one mole of (B) per mole of halogen in (A).

The reaction of this invention is best carried out at a temperature from 0° to 175° C. under autogenous pressure. The optimum temperature to be employed with any particular type of reagent varies, but in general, the higher the temperature, the less sulfide produced. The pressure, of course, will vary with the temperature and the volatility of the reactants. If desired, external pressure can be applied to the system, but this is unnecessary because the autogenous pressure is sufficient for excellent yields.

In many cases, it is advantageous to employ a polar solvent in the reaction. Examples of operative polar solvents are water, alcohols such as methanol, ethanol, isopropanol, or butanol, ethers, such as dioxane, the dimethyl ether of ethylene glycol or the monomethyl ether of ethylene glycol, nitriles such as acetonitrile, or propionitrile; N,N-disubstituted amides such as dimethyl acetamide, or diethyl formamide and sulfur compounds such as dimethyl sulfoxide. Obviously, the polar solvent should be non-acidic.

The following examples are illustrative only and should not be construed as limiting the invention which is properly delineated in the appended claims. In the examples the following abbreviations are used: Me for methyl, Et for ethyl, Pr for propyl and Ph for phenyl.

EXAMPLE 1

Trimethyl amine (37 g., 0.637 moles), hydrogen sulfide (14.1 g., 0.415 moles), and (MeO)$_3$Si(CH$_2$)$_3$Cl (72 g., 0.36 moles) were heated at 100° C. in a 300 ml. stainless steel autoclave. After 17 hours a sample was withdrawn and analyzed by glc. Chloropropyltrimethoxysilane was not detected by glc. The major product was (MeO)$_3$Si(CH$_2$)$_3$SH (97 percent glc area) with small amounts of {(MeO)$_3$Si(CH$_2$)$_3$}$_2$S$_2$ and {(MeO)$_3$Si(CH$_2$)$_3$}$_2$S.

EXAMPLE 2

A solution of equal volumes of triethyl amine and methanol were saturated with hydrogen sulfide at room temperature and atmospheric pressure. The H$_2$S was present in excess of 1 mole H$_2$S per mole of amine. 3.49 g. of n-hexyl chloride was added to 15 ml. of the above solution and the mixture was heated in a sealed container at 75° C. After 6 hours, the product was 99.1 percent n-hexyl mercaptan and 0.9 percent n-hexyl sulfide.

EXAMPLE 3

78.4 g. of ammonia and 171 g. of hydrogen sulfide were added to a three liter stainless steel autoclave. 100 ml. of methanol were pumped into the vessel followed by 819 g. of n-dodecyl chloride. This was followed by 20 ml. of methanol to flush out the pump. The sealed container was heated at 125° C. and after 22 hours gas liquid chromotography analysis showed that the product was 98.7 percent n-dodecyl mercaptan and 0.9 percent unreacted dodecyl chloride.

EXAMPLE 4

3.3 g. of ammonia was added to 31.7 ml. of methanol and then the solution was saturated with hydrogen sulfide. While continuing the hydrogen sulfide addition, 19 ml. of benzyl chloride was added and the mixture maintained at 0° C. After one hour gas liquid chromotography indicated that the product was 92 percent benzyl mercaptan and 8 percent benzyl sulfide.

EXAMPLE 5

A mixture of a saturated hydrogen sulfide solution of 12.6 g. of benzyl chloride, 8.4 g. of n-butyl amine, and 20 ml. of isopropanol was reacted at room temperature. After 15 to 30 minutes, gas liquid chromatography analysis showed that the reaction was 90 percent complete and the distribution of materials was 10 percent unreacted benzyl chloride, 82 percent benzyl mercaptan and 6 percent benzyl sulfide.

EXAMPLE 6

A solution of 10.9 g. of 1,2-dibromoethane, 13.5 g. of dipropyl amine and 10 ml. of methanol was saturated with H$_2$S and reacted at room temperature. Analysis of the product by gas liquid chromatography showed it to be 1,2-ethane dithiol. No by-products were found.

EXAMPLE 7

98 g. of ammonia, 211 g. of hydrogen sulfide and 990 g. of 3-chloropropyltrimethoxy silane were heated at 100° C. in a closed container. After 5.7 hours, the reaction was 81 percent complete and the product was 3-mercaptopropyltrimethoxy silane.

EXAMPLE 8

A mixture of 95.9 g. of ammonia, 192.2 g. of hydrogen sulfide, 970 g. of 3-chloropropyltrimethoxy silane and 150 ml. of methanol were heated in a closed container at 100° C. for 18.5 hours. The initial pressure was 195 p.s.i.g. (15.7 kg/cm²). After 18.5 hours the pressure was 85 p.s.i.g. (5.95 kg/cm²). The mixture was cooled and filtered free of ammonium chloride. The ammonium chloride was washed twice with 200 ml. portions of hexane. The original filtrate and the hexane were combined and distilled. The product was shown by gas liquid chromotography analysis to be 96.2 percent 3-mercaptopropyltrimethoxy silane, 3.2 percent unreacted chloropropyltrimethoxy silane and 0.5 percent of an unidentified impurity originally present in the chloropropyl trimethoxy silane. In other words, no sulfide was detected.

EXAMPLE 9

In an evacuated autoclave was charged 99 g. of ammonia and 198 g. of hydrogen sulfide and the autoclave was heated to 100° C. 924 g. of 3-chloropropylmethyldimethoxy silane and 100 ml. of methanol were then pumped into the autoclave and heating was continued for 26.75 hours. After cooling, the autoclave was emptied and the contents filtered free of ammonium chloride. Gas liquid chromotography analysis of the product indicated a yield of 97 percent with a 94.2 percent conversion of the chloride to the mercaptan.

EXAMPLE 10

$n\frac{25}{d}$ 1.5038, $d\frac{25}{4}$ 1.115,

Rd 0.2655, Cal. Rd 0.2666. The yield of product was 95 percent.

EXAMPLE 11

Equivalent results are obtained when cyclohexyl amine is substituted for the triethyl amine of Example 2.

EXAMPLE 12

Mercaptans are obtained when the following halides are reacted with a mixture of ammonia and $H_2S$ in the mole ratio of 1:1 at 100° C. under autogenous pressure.

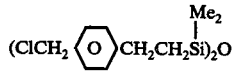

*Acid recovered by reacting with HCl.
**Run at 0° C.

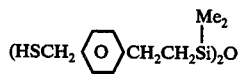

682.5 g. of a siloxane of the unit formula $Cl(CH_2)_3SiMeO$ containing 1.41 percent by weight silicon-bonded hydroxyl groups, 100 ml. of methanol, 97.5 g. of ammonia and 195.5 g. of hydrogen sulfide were mixed and heated at 125° C. for 24 hours. The initial pressure in the autoclave at 125° C. was about 500 p.s.i.g. (35.15 kg/cm²). After 24 hours, the pressure was 195 p.s.i.g. (13.6 kg/cm²). After 24 hours at 125° C., the product was cooled and diluted with ether and filtered free of ammonium chloride. The product was devolatilized at 2 mm. pressure at 60° C. for 4 hours. The resulting product was 3-mercaptopropylmethylpolysiloxane having the following properties.

EXAMPLE 13

The experiment of Example 9 was repeated with $NH_3$ (100 g., 5.88 m.), $H_2S$ (127.5 g., 3.75 m.) and methanol (100 ml.) at 100° C. $(MeO)_2MeSi(CH_2)_3Cl$ (593 g., 3.25 m.) was pumped into the autoclave followed by 100 ml. of methanol. Periodic analyses indicated:

| Time Hours | % Initial $(MeO)_2MeSi(CH_2)_3Cl$ | % $(MeO)_2MeSi(CH_2)_3SH$ |
|---|---|---|
| 0.5 | 13.1 | 85 |
| 1.5 | 5.8 | 92.1 |
| 2.5 | 2.6 | 94.7 |

This reaction was much faster than that of Example 9.

That which is claimed is:

1. A method of producing mercaptans which comprises reacting (A) a halide of the formula $RX_a$ with a mixture of (B) ammonia or a hydrocarbyl amine containing one N atom, no more than 6 carbon atoms and being free of aliphatic unsaturation and having a $K_a$ of less than $1 \times 10^{-9}$ in aqueous solution, and $H_2S$, in the mole ratio of at least one mole of $H_2S$ and one mole of (B) per mole of halogen in (A), at a temperature of from 0° to 175° C. under autogenous pressure whereby a compound of the formula $R(SH)_a$ is formed, in which process R is selected from the group consisting of aliphatic, cycloaliphatic or aralkyl hydrocarbon radicals free of aliphatic unsaturation, such hydrocarbon radicals substituted with alkoxy, keto, carboxy, hydroxyl, $-COOR^3$ or $-OOCR^3$ radicals in which $R^3$ is a monovalent hydrocarbon radical free of aliphatic unsaturation, and silylated hydrocarbon radicals of the formula $(R''O)_y R'''_{3-y} SiR^4-$ or $(O_{3-d/2})R'''_d SiR^4-$ in which R'' is an alkyl or an alkoxyalkyl radical of 1 to 6 carbon atoms, R''' is a monovalent hydrocarbon radical free of aliphatic unsaturation, a haloaryl radical or $R_f CH_2 CH_2-$ in which $R_f$ is a perfluoroalkyl radical, $R^4$ is a divalent, trivalent or tetravalent, aliphatic, cycloaliphatic or aralkyl hydrocarbon radical free of aliphatic unsaturation, $y$ is 1 to 3 and $d$ is 0 to 2, X is bromine or chlorine, and $a$ is 1 to 3.

2. The process of claim 1 which is carried out in a non-acidic, polar solvent.

3. The process of claim 1 in which (B) is ammonia.

4. The process of claim 1 in which (A) is $(R''O)_y R'''_{3-y} SiR^4-$ or $(O_{3-d/2})R'''_d SiR^4-$ and (B) is ammonia.

5. The process of claim 1 in which (A) is $(CH_3O)_n(CH_3)_{3-n}Si(CH_2)_3Cl$ where $n$ is 1 to 3 and (B) is ammonia.

6. The process of claim 2 in which (A) is $(CH_3O)_n(CH_3)_{3-n}Si(CH_2)_3Cl$ in which $n$ is 1 to 3, (B) is ammonia and the polar solvent is methanol.

7. The process of claim 6 in which $n$ is 3.

8. The process of claim 2 in which the polar solvent is methanol.

9. The process of claim 1 in which (A) is a siloxane which also contains units of the formula $R'''_z SiO_{(4-z/2)}$ in which $z$ is 0 to 3.

10. The process of claim 9 in which (B) is ammonia.

* * * * *

UNITED STATES PATENT AND TRADEMARK OFFICE
CERTIFICATE OF CORRECTION

PATENT NO. : 4,082,790
DATED : April 4, 1978
INVENTOR(S) : John L. Speier

It is certified that error appears in the above-identified patent and that said Letters Patent are hereby corrected as shown below.

In Column 8, lines 13 and 14; the formula reading

"$(R"O)_y R'''\lambda_{3-y} SiR^4-$" should read "$(R"O)_y R'''_{3-y} SiR^4-$".

Signed and Sealed this

First Day of December 1981

[SEAL]

Attest:

GERALD J. MOSSINGHOFF

Attesting Officer      Commissioner of Patents and Trademarks